United States Patent [19]
Arndt

[11] Patent Number: 5,451,699
[45] Date of Patent: Sep. 19, 1995

[54] PROCESS FOR THE PREPARATION OF CRYSTALLINE, SALT-FREE, CHLORINE-SUBSTITUTED 3-NITROBENZENESULFONIC ACID HYDRATES

[75] Inventor: Otto Arndt, Hofheim, Germany

[73] Assignee: Hoechst AG, Frankfurt, Germany

[21] Appl. No.: 223,635

[22] Filed: Apr. 6, 1994

[30] Foreign Application Priority Data

Apr. 6, 1993 [DE] Germany .................. 43 11 381.8

[51] Int. Cl.$^6$ ............................................. C07C 309/29
[52] U.S. Cl. ................................................... 562/73
[58] Field of Search ........................................ 562/73

[56] References Cited

U.S. PATENT DOCUMENTS 4,242,275 12/1980 Arndt et al. .

FOREIGN PATENT DOCUMENTS 86391 12/1971 Germany .
2621168 11/1977 Germany .
3501754 7/1986 Germany .

*Primary Examiner*—Nicky Chan
*Attorney, Agent, or Firm*—Connolly and Hutz

[57] ABSTRACT

The present invention relates to a process for the preparation of crystalline, salt-free, chlorine-substituted 3-nitrobenzenesulfonic acid hydrates from sulfonation mixtures containing chlorine-substituted 3-nitrobenzenesulfonic acid, in which the sulfonation mixture is mixed with from 8 to 25% strength by weight aqueous sulfuric acid at from 40° C. to 100° C., the resulting suspension is cooled to from 5° C. to 20° C., the precipitate is filtered off and dissolved with water at from 30° C. to 100° C., filtration is carried out if desired, the solution is cooled to from 5° to 40° C. and filtered, and the sulfuric acid-containing filtrate is recycled if desired.

17 Claims, No Drawings

PROCESS FOR THE PREPARATION OF CRYSTALLINE, SALT-FREE, CHLORINE-SUBSTITUTED 3-NITROBENZENESULFONIC ACID HYDRATES

The invention relates to a process for the preparation of crystalline, salt-free, chlorine-substituted 3-nitrobenzenesulfonic acid hydrates from sulfonation mixtures containing chlorine-substituted 3-nitrobenzenesulfonic acid.

The preparation of chlorine-substituted 3-nitrobenzenesulfonic acids is described in the literature (e.g. Ullmann, Encyclopädie der technischen Chemie [Encyclopedia of Industrial Chemistry], 4th edition 1979, volume 17, pp. 405–408). Both batchwise and continuous processes are known, on the one hand for the nitration of the corresponding benzenesulfonic acids and on the other hand for the sulfonation of the corresponding nitrobenzenes. Because of the lower safety risk, the sulfonation processes are preferred over the nitration processes.

The corresponding 3-nitrobenzenesulfonic acids can be isolated in the form of their sodium salts by mixing the reaction mixtures with water and sodium hydroxide or calcium hydroxide and NaCl. A problem of this procedure is that the formation of large quantities of sodium sulfate and calcium sulfate lead to a high salt loading of the waste water. Isolation as the free acid is therefore more advantageous. For this purpose the reaction mixtures are combined with water or- to reduce the heat of mixing- with aqueous sulfuric acid, the free sulfonic acids crystallizing out. They are isolated by filtration.

GDR Patent 86 391 describes a process of this kind for the continuous production of 4-nitrotoluene-2-sulfonic acid from a sulfonation mixture to which 40 to 50% strength aqueous sulfuric acid is added.

However, in this procedure, which is restricted to the production of 4-nitrotoluene-2-sulfonic acid, the product obtained retains a large quantity of sulfuric acid.

Given the objective not only of obtaining a product of maximum purity but also of supplying as high as possible a proportion of the waste sulfuric acid for reprocessing and/or reuse, the process described in GDR Patent 86 391 leaves something to be desired.

The object was to develop a process which corresponds to the abovementioned objective, can be applied to chlorine-substituted 3-nitrobenzenesulfonic acids and furthermore whose industrial implementation is simple.

This object is achieved by a process for the preparation of crystalline, salt-free, chlorine-substituted 3-nitrobenzenesulfonic acid hydrates from sulfonation mixtures which contain chlorine-substituted 3-nitrobenzenesulfonic acid. The process comprises mixing the sulfonation mixture with from 8–25% by weight strength aqueous sulfuric acid at from 40° C. to 100° C., cooling the resulting suspension to from 5° C. to 20° C., filtering off the precipitate and dissolving it with water at from 30° C. to 100° C., carrying out filtration if desired, cooling the solution to from 5° to 40° C., preferably to from 10 to 40° C., and filtering it, and recycling the sulfuric acid-containing filtrate if desired. In view of the good solubility of sulfonic acids in water, it is particularly surprising here that the loss in yield caused by the additional process step is only minimal.

The process according to the invention results, on the one hand, in chlorine-substituted 3-nitrobenzenesulfonic acid hydrates in highly pure form and, on the other hand, in a very high proportion of reprocessable sulfuric acid. From the sulfonic acid hydrates it is not difficult to prepare either the free sulfonic acid or salts of sulfonic acids. Owing to its preparation, the sulfonation mixture contains usually concentrated sulfuric acid and/or oleum. The addition of dilute aqueous sulfuric acid dilutes the concentrated sulfuric acid and converts the oleum to sulfuric acid. This precipitates the chlorine-substituted 3-nitrobenzenesulfonic acid in hydrate form, which is filtered off. The resulting fraction of sulfuric acid, because of its sulfuric acid content (from about 40 to 50% by weight sulfuric acid) is particularly suitable for regeneration. The hydrate of the chlorine-substituted 3-nitrobenzenesulfonic acid, which is precipitated from the sulfonation mixture by the addition of dilute aqueous sulfuric acid and the subsequent cooling of the suspension, is filtered off and then dissolved in hot water. This aqueous solution is cooled, advantageously in two steps, and filtered to remove the chlorine-substituted 3-nitrobenzenesulfonic acid hydrate which is precipitated. The sulfuric acid-containing filtrate obtained when the hydrate is filtered off can be used with particular advantage for mixing with the sulfonation mixture, the sulfuric acid which is obtained again being supplied for regeneration. In this way the sulfuric acid obtained can be used rationally to a very great extent while very largely avoiding the formation of unwanted, waste sulfuric acid which cannot be reprocessed. The process is suitable for a sulfonation mixture which contains 6-chloro-3-nitrobenzenesulfonic acid or 4-chloro-3-nitrobenzenesulfonic acid, especially 6-chloro-3-nitrobenzenesulfonic acid, as the chlorine-substituted 3-nitrobenzenesulfonic acid.

In many cases it is advisable to mix the sulfonation mixture with from 10 to 20% by weight strength, in particular from 10 to 15% by weight strength, aqueous sulfuric acid at a temperature of from 40° C. to 75° C., in particular from 45° C. to 65° C. and preferably from 50° C. to 60° C.

The majority of the heat liberated during precipitation is absorbed by the sulfuric acid used for dilution. The cooling can therefore be controlled with ease.

In many cases it has proven suitable to cool the suspension which is obtained to from 10° to 18° C., preferably from 12° to 16° C., to dissolve the resulting precipitate in water at from 45° C. to 80° C., preferably from 50° to 60° C., and to cool the resulting solution initially to from 25° to 35° C. and subsequently to from 5° to 15° C. Both batchwise and continuous procedures-can be adopted for the process.

The process according to the invention is illustrated by the following example, without being restricted thereto.

EXAMPLE 1

1a) Preparation of the crude dihydrate (1st precipitation)

158.4 parts by weight of a sulfonation mixture (density 1.64 g/ml) which is obtained by reacting 63.0 parts by weight of 4-chloronitrobenzene with 86.3 parts by weight of 65% strength oleum (=65 parts of $SO_3$ and 35 parts of $H_2SO_4$) and 9.1 parts by weight of $H_2SO_4$ is mixed, in an enameled dilution and precipitation vessel which is equipped with an anchor stirrer and cooling means, with 180.0 parts by weight of 11% strength sulfuric acid (or dilute sulfuric acid filtrate from the 2nd precipitation) at 50°–60° C., with high-speed stirring and moderate external cooling. After a residence time of about 2 hours at 50°–60° C. with stirring, the thin suspension is run into an enameled after stirring vessel which is equipped with an anchor stirrer and cooling means and where, after a residence time of at least 5 hours at 15° C., crystallization is brought to completion, again with stirring. The thin suspension, which has a solid content of 31%, is filtered to isolate the solids. About 163.0 parts by weight are obtained of industrially moist 6-chloro-3-nitrobenzenesulfonic acid dihydrate, containing 103.0 parts by weight of 6-chloro-3-nitrobenzenesulfonic acid and 21.0 parts by weight of $H_2SO_4$ (each calculated as 100% pure).

The filtrate (150.8 parts by weight with a density of 1.36) is 44% strength sulfuric acid containing 66.6 parts by weight of $H_2SO_4$ (calculated as 100% pure).

1.5 parts by weight of the filtrate are withdrawn as recycled sulfuric acid, and are combined with sulfuric acid filtrate from the 2nd precipitation.

The main proportion of the filtrate (149.3 parts by weight, containing 65.8 parts by weight of $H_2SO_4$ (calculated as 100% pure, corresponding to 96% of the total waste sulfuric acid)) goes for regeneration.

The industrially moist 6-chloro-3-nitrobenzenesulfonic acid dihydrate is passed directly into the enameled vessel, equipped with an anchor stirrer and cooling means, for the 2nd precipitation.

1b) 2nd precipitation 80.0 parts by weight of water at 50° C. are charged initially and 163.0 parts by weight of industrially moist 6-chloro-3-nitrobenzenesulfonic acid dihydrate are introduced with stirring. The mixture is heated to 50° C. All of the solid—apart from the sulfone, which remains as a solid—dissolves. The mixture is stirred slowly and left to crystallize, initially at about 30° C., and is then cooled to 10° C. using cooling brine. Stirring is continued for 1 hour. The readily stirrable suspension is filtered to remove solids at 10° C.

120.0 parts by weight are obtained of industrially moist 6-chloro-3-nitrobenzenesulfonic acid dihydrate, containing 106.0 parts by weight of 6-chloro-3-nitrobenzenesulfonic acid dihydrate (=92.0 parts by weight of 6-chloro-3-nitrobenzenesulfonic acid) and 3.0 parts by weight of $H_2SO_4$, each calculated as 100% pure, and also 25.0 parts by weight of water.

The sulfuric acid filtrate running off (=115.0 parts by weight) contains 10.4 parts by weight of 6-chloro-3-nitrobenzenesulfonic acid and 19.0 parts by weight of $H_2SO_4$, each calculated as 100% pure. The filtrate is adjusted to a content of 19.6 parts by weight of 100% pure $H_2SO_4$. The make-up quantity of sulfuric acid depends on the sulfuric acid content of the sulfuric acid filtrate resulting from the crystallization.

About 62.5 parts by weight of water are used to dilute the sulfuric acid filtrate to a quantity of 180.0 parts by weight (density =1.10 g/ml, $H_2SO_4$ content =10.9% by weight).

The resulting acid is employed for mixing with further sulfonation mixture and for precipitating further 6-chloro-3-nitrobenzenesulfonic acid dihydrate.

I claim:

1. A process for the preparation of crystalline, salt-free, chlorine-substituted 3-nitrobenzenesulfonic acid hydrates from sulfonation mixtures which contain a chlorine-substituted 3-nitrobenzenesulfonic acid, which comprises mixing the sulfonation mixture with from 8–25% by weight strength aqueous sulfuric acid at from 40° C. to 100° C., cooling the resulting suspension to from 5° C. to 20° C., filtering off the precipitate and dissolving it with water at from 30° C. to 100° C., optionally carrying out filtration, cooling the solution to from 5° to 40° C. and optionally filtering it, and optionally recycling the sulfuric acid-containing filtrate.

2. The process as claimed in claim 1, wherein the sulfonation mixture contains 6-chloro-3-nitrobenzenesulfonic acid or 4-chloro-3-nitrobenzenesulfonic acid as chlorine-substituted 3-nitrobenzenesulfonic acid.

3. The process as claimed in claim 1, wherein the sulfonation mixture is mixed with from 10 to 20% strength by weight aqueous sulfuric acid.

4. The process as claimed in claim 1, wherein the sulfonation mixture is mixed with aqueous sulfuric acid at from 45° to 65° C.

5. The process as claimed in claim 1, wherein the suspension which is obtained is cooled to from 10° to 18° C.

6. The process as claimed in claim 1, wherein the precipitate is dissolved with water at from 50° to 60° C.

7. The process as claimed in claim 1, wherein the solution is cooled initially to from 25° to 35° C. and subsequently to from 5° to 15° C.

8. The process as claimed in claim 1, wherein the sulfuric-acid containing filtrate comprises 8–25% by weight strength aqueous sulfuric acid, and said filtrate is recycled to the mixing step of said process, where it is mixed with the sulfonation mixture.

9. The process as claimed in claim 1, wherein the sulfonation mixture has been obtained by sulfonating a chlorine-substituted 3-nitrobenzene with a sulfonating agent containing oleum or concentrated sulfuric acid.

10. The process as claimed in claim 9, wherein the mixing of the sulfonation mixture with the 8–25% by weight strength aqueous sulfuric acid dilutes said concentrated sulfuric acid or converts said oleum to sulfuric acid and precipitates said chlorine-substituted 3-nitrobenzene sulfonic acid in hydrate form.

11. A process for the preparation of a crystalline, essentially salt-free, chlorine-substituted 3-nitrobenzenesulfonic acid hydrate from a sulfonation mixture which contains a chlorine-substituted 3-nitrobenzenesulfonic acid and oleum or concentrated sulfuric acid or a mixture of oleum and sulfuric acid, comprising:

mixing the sulfonation mixture with 10 to 20 weight-% strength aqueous sulfuric acid at from 40° C. to 100° C. to precipitate a said chlorine-substituted 3-nitrobenzenesulfonic acid, thereby obtaining a suspension containing said precipitate, cooling said suspension to from 5° C. to 20° C. and recovering chlorine-substituted nitrobenzenesulfonic in solid hydrate form, dissolving the thus-recovered hydrate in water at from 30° C. to 100° C. to obtain an aqueous solution containing a chlorine-substituted 3-nitrobenzenesulfonic acid, cooling said aqueous solution to from 5° to 40° C. and filtering said aqueous solution to recover a chlorine-substituted 3-nitrobenzenesulfonic acid hydrate.

12. The process as claimed in claim 11, wherein the sulfonation mixture contains 6-chloro-3-nitrobenzenesulfonic acid.

13. The process as claimed in claim 11, wherein said mixing step is carried out with 10 to 15 weight-% strength aqueous sulfuric acid.

14. The process as claimed in claim 11, wherein said mixing step is carried out at 45° to 65° C.

15. The process as claimed in claim 11, wherein said suspension is cooled to 12° to 16° C.

16. The process as claimed in claim 11, wherein the filtering of said aqueous solution to recover a chlorine-substituted 3-nitrobenzene-sulfonic acid hydrate provides an aqueous filtrate containing 8 to 25 weight-% sulfuric acid.

17. The process as claimed in claim 16, wherein said aqueous filtrate is recycled to said mixing step of said process.

* * * * *